(12) United States Patent
Huang et al.

(10) Patent No.: US 9,878,967 B2
(45) Date of Patent: Jan. 30, 2018

(54) METHOD OF CONVERTING LEVULINIC ACID OR A DERIVATIVE THEREOF TO HYDROCARBONS AND HYDROGEN, AND METHODS OF THE PRODUCTION OF HYDROCARBONS AND HYDROGEN

(71) Applicant: Iowa State University Research Foundation, Inc., Ames, IA (US)

(72) Inventors: Wenyu Huang, Ames, IA (US); Chaoxian Xiao, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/387,924

(22) Filed: Dec. 22, 2016

(65) Prior Publication Data

US 2017/0183274 A1 Jun. 29, 2017

Related U.S. Application Data

(60) Provisional application No. 62/387,158, filed on Dec. 23, 2015.

(51) Int. Cl.
*C07C 1/20* (2006.01)
*C07C 1/207* (2006.01)
*C10G 1/00* (2006.01)

(52) U.S. Cl.
CPC ........ *C07C 1/2078* (2013.01); *C07C 2101/10* (2013.01); *C07C 2101/16* (2013.01); *C07C 2521/06* (2013.01); *C07C 2521/08* (2013.01); *C07C 2521/18* (2013.01); *C07C 2523/10* (2013.01); *C07C 2523/28* (2013.01); *C07C 2523/42* (2013.01); *C07C 2523/745* (2013.01); *C07C 2523/75* (2013.01); *C07C 2523/755* (2013.01); *C07C 2523/835* (2013.01); *C07C 2523/89* (2013.01)

(58) Field of Classification Search
CPC .............. C10G 1/00; C07C 1/20; C07C 1/207
USPC ....... 585/240, 242, 319, 324, 357, 469, 638, 585/639, 640, 733
See application file for complete search history.

(56) References Cited

U.S. PATENT DOCUMENTS 6,617,464 B2  9/2003 Manzer
7,880,049 B2  2/2011 Dumesic et al.
8,362,306 B2  1/2013 Wheeler et al.
2010/0312006 A1  12/2010 Lake et al.
2010/0324310 A1* 12/2010 Dumesic .............. B01J 23/6484
                                                      549/326
2013/0217932 A1  8/2013 Seck

FOREIGN PATENT DOCUMENTS

WO  2007/099111 A1  9/2007
WO  2008/151178 A1  12/2008
WO  2010/151343 A1  12/2010
WO  2015/026234 A1  2/2015

OTHER PUBLICATIONS

Bond et al., "Integrated Catalytic Conversion of Gamma-Valerolactone to Liquid Alkenes for Transportation Fuels," Science 327:1110-1114 (2010).
Braden et al., "Production of Liquid Hydrocarbon Fuels by Catalytic Conversion of Biomass-Derived Levulinic Acid," Green Chem. 13:1755-1765 (2011).
Case et al., "Liquid Hydrocarbon Fuels From Cellulosic Feedstocks via Thermal Deoxygenation of Levulinic Acid and Formic Acid Salt Mixtures," Green Chem. 14:85-89 (2012).
Corma et al., "Conversion of Levulinic Acid Derived Valeric Acid Into a Liquid Transportation Fuel of the Kerosene Type," Journal of Molecular Catalysis A: Chemical 388-389:116-122 (2014).
Huang, "Liquid Phase Refining of Biomass to Fuels by Graphene Derived Nanocatalysts," Iowa State University Public Grant Abstract 2012.
Serrano-Ruiz et al., "Catalytic Upgrading of Levulinic Acid to 5-Nonanone," Green Chem. 12:574-577 (2010).
Schwartz et al., "Energy Densification of Levulinic Acid by Thermal Deoxygenation," Green Chem. 12:1353-1356 (2010).
Karimi et al., "Ketonization and Deoxygenation of Alkanoic Acids and Conversion of Levulinic Acid to Hydrocarbons Using a Red Mud Bauxite Mining Waste as the Catalyst," Catalyst Today 190:73-88 (2012).
Mascal et al., "Hydrodeoxygenation of the Angelica Lactone Dimer, a Cellulose-Based Feedstock: Simple, High-Yield Synthesis of Branched C7-C10 Gasonline-Like Hydrocarbons," Angew. Chem. Int. Ed. 53:1854-1857 (2014).

* cited by examiner

*Primary Examiner* — Thuan D Dang
(74) *Attorney, Agent, or Firm* — LeClairRyan, a Professional Corporation (57) ABSTRACT

The present invention relates to a method of converting levulinic acid or a derivative thereof to hydrocarbons and hydrogen by providing a source of levulinic acid or a derivative thereof and converting the levulinic acid or a derivative thereof in the source to hydrocarbons and hydrogen, where converting is carried out in a single reactor. The present invention also relates to methods for producing hydrocarbons and hydrogen.

29 Claims, 6 Drawing Sheets

FIG. 1

Typical olefins and aromatics (majority):

Typical oxygenates (~3wt%):

METHOD OF CONVERTING LEVULINIC ACID OR A DERIVATIVE THEREOF TO HYDROCARBONS AND HYDROGEN, AND METHODS OF THE PRODUCTION OF HYDROCARBONS AND HYDROGEN

This application claims priority benefit of U.S. Provisional Patent Application Ser. No. 62/387,158, filed Dec. 23, 2015, which is hereby incorporated by reference in its entirety.

FIELD OF THE INVENTION

The present invention relates to a method of converting levulinic acid or a derivative thereof to hydrocarbons and hydrogen and methods of producing hydrocarbons and hydrogen.

BACKGROUND OF THE INVENTION

Lignocellulosic biomass residues, such as corn stover and wheat straw, typically contain about 30-45 wt % cellulose, 15-30 wt % hemicellulose, and 10-25 wt % lignin (Huber et al., "Synthesis of Transportation Fuels from Biomass: Chemistry, Catalysts, and Engineering," *Chemical Reviews* 106:4044-4098 (2006)). These low value materials (deliverable at about $50/dry ton) (*EPA Combined Heat and Power Partnership: Biomass CHP Catalog* 14, Sep. 18, 2013) are currently underutilized, and could be converted to higher value bio-based products and biofuels through various pathways (Huber et al., "Synthesis of Transportation Fuels from Biomass: Chemistry, Catalysts, and Engineering," *Chemical Reviews* 106:4044-4098 (2006); Brown et al., "A Review of Cellulosic Biofuel Commercial-Scale Projects in the United States," *Biofuels, Bioprod. Biorefin.* 7:235-245 (2013)).

The production of advanced "drop in" hydrocarbon fuels has received intense interest (Brown et al., "A Review of Cellulosic Biofuel Commercial-Scale Projects in the United States," *Biofuels, Bioprod. Biorefin.* 7:235-245 (2013)). The primary motivation of the biofuel industry includes a vast market capacity ($99 billion in 2014) (PRNewswire http://www.prnewswire.com/(2014)), minimizing the dependence on foreign petroleum, decreasing greenhouse emissions, and creating jobs. Existing technologies for the production of "drop in" biofuels include fermentation, pyrolysis, gasification, and liquid phase refinery approaches. However, the main problem with these existing technologies is that the production costs of advanced "drop in" fuels is too high to compete with conventional fuels. Novel technologies that can address economic and environmental problems are highly demanded.

Levulinic acid, or 4-oxopentanoic acid, can be produced in high yield through acid-catalyzed dehydration and hydrolysis of hexose sugars. Levulinic acid has also been identified by the U.S. Department of Energy as one of the "top 10" platform molecules derived from cellulosic biomass. The production of levulinic acid from carbohydrates in the presence of mineral acids has been practiced in a long history since Dutch professor G. J. Mulder first discovered this process in the 1840's. When treated at 140-210° C. for several hours in the presence of 1-5 wt % sulfuric acid (Rackemann et al., "The Conversion of Lignocellulosics to Levulinic Acid," *Biofuels, Bioprod. Biorefin.* 5:198-214 (2011)), cellulose first depolymerizes into 5-hydroxymethylfurfural (HMF), followed by hydration and decomposition to form levulinic acid and formic acid in approximately equal molar amounts. Excellent yield (70-80% of the theoretical yield) could be obtained from various biomass feedstocks, such as corn stover, wheat straw, pine saw dust, etc. Meanwhile, furfural can also be obtained from the conversion of hemicellulose with ~70% yield in this process. Furfural can be sold as a higher-value byproduct at a market price of ~$1,000/dry ton. Some amount of humin (carbonaceous solids) could be generated as the byproduct. Biofine Inc. has proposed that humin can be utilized as valuable fuel to provide heat for an entire facility. The production cost of levulinic acid has been estimated to be ~$0.04-$0.1 per pound if produced at a sufficiently large scale (~1,000 dry ton/day).

The aqueous broth obtained from the above-mentioned acid-treating process typically contains 5 wt % levulinic acid and 2 wt % formic acid. Traditional methods developed by Biofine Inc. utilize lime to neutralize sulfuric acid, followed by distillation to separate water, formic acid, and levulinic acid. This process consumes lime and sulfuric acid and produces gypsum (calcium sulfate) as a low-value by-product. Thus, it is neither energy efficient nor environmentally friendly (Kamm et al., *Biorefineries—Industrial Processes and Products in Ullmann's Encyclopedia of Industrial Chemistry*, 659-688 (WILEY-VCH Verlag GmbH & Co. KGaA, Weinheim (2006)).

Hence, other energy-saving approaches for the separation of levulinic acid and formic acid from aqueous solution have been explored. The most promising method is extraction. Suitable solvents for this purpose include chloroform, ethers, alcohols, esters, ketones, hydrocarbons, and ternary amines.

Hydrogen is very important in the conversion of biomass to hydrocarbons because biomass usually contains highly oxygenated compounds that require a further hydrotreating process to remove excessive oxygen content. However, the production of hydrogen requires an additional facility that could increase capital and operation costs at a significant level. Thus, co-production of hydrogen along with hydrocarbons is of importance to reduce production cost in a biorefinery. However, there are no known techniques that could produce hydrocarbons and hydrogen together from levulinic acid and its derivatives, particularly in one process.

There are several existing technologies for the production of solely hydrocarbons from levulinic acid that generally employ multiple processing steps. For instance, Dumesic developed a three-step process to convert levulinic acid to C8+ olefins (Bond et al., "Integrated Catalytic Conversion of γ-Valerolactone to Liquid Alkenes for Transportation Fuels," *Science* 327:1110-1114 (2010); Bond et al., "Production of Renewable Jet Fuel Range Alkanes and Commodity Chemicals from Integrated Catalytic Processing of Biomass," *Energy Environ. Sci.* 7:1500-1523 (2014); PCT Publication No. WO/2008/151178). First, gamma-valerolactone ("GVL") was obtained from the hydrogenation of levulinic acid using RuSn catalyst. Second, gamma-valorolactone was passed through a silica-alumina catalyst to produce butenes after decarboxylation. Third, C8, C12, and C16 olefins were produced through oligomerization of butenes using HZSM-5 or Amberlyst-70 solid acid catalyst. The total yields of C8-C16 olefins are approximately 50-60%. This process does not need additional hydrogen, but uses a noble metal (Ru) catalyst and employs three steps. The same group also developed a process to convert gamma-valerolactone to 5-nonanone via hydrogenation, decarboxylation, and coupling reactions using Pd/Nb$_2$O$_5$ catalyst. The total yield of 5-nonanone is approximately 60%. However, 5-nonanone has to be further upgraded through a hydrodeoxygenation reaction to obtain hydrocarbons which are suitable to be used as diesel and gasoline. The main drawback of this process is that an additional hydrogen production facility is required, and so is the use of a noble metal catalyst.

Another approach developed by Mascal can produce C7-C10 hydrocarbons (primarily gasoline components) from levulinic acid (Mascal et al., "Hydrodeoxygenation of the Angelica Lactone Dimer, a Cellulose-Based Feedstock: Simple, High-Yield Synthesis of Branched C-7-C-10 Gasoline-like Hydrocarbons," *Angew Chem. Int. Ed. Engl.* 53:1854-1857 (2014)). The total yield is approximately 73%. But the process includes three steps (dehydration, coupling reaction, and hydrogenation). This process also requires the construction of an additional hydrogen supply facility that may increase capital costs by 50%.

Another process employs thermal treatment to convert dry calcium levulinate to produce a mixture of hydrocarbons and ketones in one pass (Schwartz et al., "Energy Densification of Levulinic Acid by Thermal Deoxygenation," *Green Chem.* 12:1353 (2010)). However, the yield of this process is not reported, and an additional neutralization step to convert levulinic acid to calcium levulinate with lime is required. The main drawback of this process is that water has to be removed from levulinic acid feedstock, and there is a high energy input demand owing to a high reaction temperature (450° C.).

Another approach can produce GVL, pentanoic acid, butenes/butanes from the total deoxygenation of levulinic acid in the presence of trifluoromethylsulfonic acid and 316 stainless steel powder catalyst (Elham et al., "Stainless Steel As a Catalyst for the Total Deoxygenation of Glycerol and Levulinic Acid in Aqueous Acidic Medium," *ACS Catalysis* 1.355 (2011)). They proposed that 316 stainless steel could act as the catalyst for this process. However, they did not report the production of higher hydrocarbons (>4 carbon atoms) that are suitable for use as transportation fuels.

Another approach can produce linear C9 ketones (nonane) through ketonization of levulinic acid with alkaline red mud catalyst. According to this approach it was proposed that linear chain hydrocarbons could be obtained with further hydrogenation of linear C9 ketones. As such, in the presence of red mud catalyst (primarily composed of iron, titanium dioxide, alumina, silica), external hydrogen supply at significantly high temperatures (365° C.), an organic phase being primarily composed of the desired linear C9 total deoxygenation products of the reaction cascade starting with LA ketonization along with some of the corresponding alcohols was obtained by the hydrogenation of C9 ketone derived from the upgrading of levulinic acid. They did not report the presence of cycloalkenes and hydrogen. When no catalyst and no hydrogen was applied, the yield of organic phase product was rather low (<10%) (Elham et al., "Ketonization and Deoxygenation of Alkanoic Acids and Conversion of Levulinic Acid to Hydrocarbons Using a Red Mud Bauxite Mining Waste as the Catalyst," *Catalysis Today* 190:73-88 (2012)). The main drawback of this process is a high reaction temperature and no production of hydrogen.

The present invention is directed to overcoming these and other deficiencies in the art.

SUMMARY OF THE INVENTION

One aspect of the present invention relates to a method of converting levulinic acid or a derivative thereof to hydrocarbons and hydrogen. This method involves providing a source of levulinic acid or a derivative thereof and converting levulinic acid or a derivative thereof in the source to hydrocarbons and hydrogen, where said converting is carried out in a single reactor.

Another aspect of the present invention relates to a method of producing hydrocarbons and hydrogen. This method involves providing a reactor that includes levulinic acid or a derivative thereof, water, and formic acid. The reactor or contents therein are heated under conditions effective to convert the levulinic acid or derivative thereof to hydrocarbons and hydrogen.

Another aspect of the present invention relates to a method of producing hydrogen. This method involves providing a reactor that includes levulinic acid or a derivative thereof, water, and formic acid. The reactor or contents therein are heated under conditions effective to convert the levulinic acid or a derivative thereof, water, and formic acid to hydrogen.

Yet another aspect of the present invention relates to a method for producing hydrocarbons and hydrogen from biomass. This method involves providing lignocellulosic biomass; reacting the biomass with reagents under conditions effective to produce levulinic acid or a derivative thereof; and converting the levulinic acid or derivative thereof to hydrocarbons and hydrogen, where said converting is carried out in a single reactor.

A further aspect of the present invention relates to a method for producing hydrocarbons and hydrogen from biomass. This method involves providing lignocellulosic biomass; reacting the biomass with reagents under conditions effective to produce levulinic acid or a derivative thereof; providing a reactor that includes the levulinic acid or a derivative thereof, water, and formic acid; and heating the reactor or contents therein under conditions effective to convert the levulinic acid or derivative thereof to hydrocarbons and hydrogen.

The present application relates to a process that can produce olefins and aromatics in a mixture in only two steps from cellulose. The products are suited for making polymer precursors, gasoline, aviation fuel, diesel, and lubricants as replacements of petroleum-based products.

DETAILED DESCRIPTION OF THE INVENTION

Disclosed herein is a method of converting levulinic acid or a derivative thereof to hydrocarbons and hydrogen, and methods of the production of hydrocarbons and hydrogen in the same process.

One aspect of the present invention relates to a method of converting levulinic acid or a derivative thereof to hydrocarbons and hydrogen. This method involves providing a source of levulinic acid or a derivative thereof and converting levulinic acid or a derivative thereof in the source to hydrocarbons and hydrogen, where said converting is carried out in a single reactor.

Levulinic acid is a well-known compound having the following chemical structure:

Levulinic acid derivatives are also well-known and include, without limitation, esters of levulinic acid (e.g., levulinate ester), salts of levulinic acid (e.g., ammonium levulinate), amides of levulinic acid, acid halides of levulinic acid, nitriles of levulinic acid, and anhydrides of levulinic acid.

In one embodiment, this and other aspects of the present invention are carried out to convert levulinic acid to hydrocarbons and hydrogen. In another embodiment, this and other aspects of the present invention are carried out to convert levulinate ester (or another levulinic acid derivative, or a mixture of levulinic acid derivatives) to hydrocarbons and hydrogen. In a further embodiment, this and other aspects of the present invention are carried out to convert a mixture of levulinic acid and one or more levulinic acid derivatives to hydrocarbons and hydrogen.

As used herein the term "source of levulinic acid or a derivative thereof" or "source" refers to a starting material for carrying out this and other methods of the present invention. Suitable sources of levulinic acid or a derivative thereof include any material that contains levulinic acid or a levulinic acid derivative and can be used as a starting material in carrying out this and other methods of the present invention. According to one embodiment, the "source of levulinic acid or a derivative thereof" is pure or substantially pure levulinic acid, pure or substantially pure derivative of levulinic acid, pure or substantially pure mixture of derivatives of levulinic acid, or pure or substantially pure mixture of levulinic acid and one or more derivatives of levulinic acid. In one embodiment, filtration, liquid-liquid extraction, or distillation is used to generate a source of levulinic acid or a derivative thereof to separate levulinic acid or a derivative thereof from carbon precipitates, water, mineral acid catalyst, and/or furfural. According to another embodiment, the source of levulinic acid or a derivative thereof is not pure or substantially pure, but contains an amount of levulinic acid or a derivative thereof sufficient as a starting material in carrying out this and other methods of the present invention.

According to one embodiment, a suitable but non-limiting source of levulinic acid or a derivative thereof is biomass material, such as cellulosic biomass or lignocellulosic biomass. As used herein, the terms "biomass," "cellulosic biomass," or "lignocellulosic biomass" refer to any plant material, vegetation, or vegetative agricultural waste from any source that can be used to supply carbohydrates to be used as reactants in any of the methods of the present invention where a source of levulinic acid or a derivative thereof is used. Exemplary cellulosic biomass includes, without limitation, corn stover, sugarcane bagasse, wheat straw, saw mill and paper mill discards (e.g., pine saw dust), and energy crops (e.g., switch grass) which are known to give high yield of levulinic acid. Energy crops are crops with high yield of lignocellulosic biomass produced to serve as a raw material for production of second generation biofuel. Suitable non-limiting examples include switch grass (*Panicum virgatum*), sorghum, and Elephant grass.

In one embodiment, it may be desirable to purify or partly purify the biomass to a higher concentration of levulinic acid or a derivative thereof than what naturally exists in the biomass. For example, methods of obtaining levulinic acid from cellulosic biomass are well known and include, without limitation, the methods described in U.S. Pat. No. 6,054,611 to Farone and Cuzens, which is hereby incorporated by reference in its entirety.

Accordingly, in carrying out this and other methods of the present invention, "providing" a source of levulinic acid or a derivative thereof, is meant that the source of levulinic acid or a derivative thereof is used as a starting material for carrying out a reaction that converts levulinic acid or a derivative thereof to hydrocarbons and hydrogen. The source of levulinic acid or a derivative thereof may be provided as a pure or substantially pure source, as discussed supra, or a solution or mixture containing levulinic acid or a derivative thereof in something other than a pure or substantially pure form. By "providing" it is also meant that the source of levulinic acid or a derivative thereof is in a reactor, placed in a reactor, or capable of being introduced into a reactor to carry out this and other methods of the present invention.

As used herein, "converting" levulinic acid or a derivative thereof means using the source of levulinic acid or a derivative thereof as the starting material in a chemical reaction that chemically converts the levulinic acid or derivative thereof to hydrocarbons and hydrogen.

According to this and other aspects of the present invention, converting levulinic acid or a derivative thereof is carried out in a single reactor. A significant achievement of the present invention is in converting levulinic acid or a derivative thereof to hydrocarbons and hydrogen together in a single reactor, without having to separate reactants, carry out multiple processing steps, or use multiple reactors to achieve the desired product (i.e., hydrocarbons and hydrogen). In other words, the source of levulinic acid or a derivative thereof is directly converted to hydrocarbons and hydrogen without having to carry out multiple reaction steps in multiple reactors or reactor chambers, as has historically been the case. Instead, converting levulinic acid or a derivative thereof to hydrocarbons and hydrogen, according to this and other aspects of the present invention, occurs in a single reactor, pot, or reaction chamber, without it being necessary to transfer reactants or products from one reactor or reaction chamber to another to carry out multiple reaction or processing steps.

In carrying out this and other methods of the present invention, the reactor can include a high pressure vessel (e.g., a sealed reactor), a batch reactor, or a continuous flow reactor. In one embodiment, the reactor used in carrying out this and other methods of the present invention is a high pressure vessel. In another embodiment, the reactor used in carrying out this and other methods of the present invention is a continuous flow reactor. In a continuous flow reactor, material (e.g., a source of levulinic acid or a derivative thereof) flows as a stream through the reactor, and reactants are continuously fed into the reactor and emerge as a stream of product. The continuous flow reactor is operated at elevated pressures. Alternatively, the reactor is not a continuous flow reactor, and the method is carried out by converting levulinic acid or a derivative thereof according to batch production.

In one embodiment of this and other methods of the present invention, converting levulinic acid or a derivative thereof in the source to hydrocarbons and hydrogen is carried out in the presence of a catalyst, although a catalyst is not required to carry out the method of this and other aspects of the present invention. When used, a suitable catalyst may include, without limitation, a metal, metal oxide, zeolite, or a mixture thereof. For example, the catalyst may be selected from the group consisting of V, Cr, Mn, Fe, Co, Ni, Cu, Mo, Ru, Ag, W, Pt, and Sn. In one particular embodiment, the catalyst is selected from Fe, Co, Ni, Ru, Sn, Mo, Pt, or mixture thereof.

In one embodiment, converting levulinic acid or a derivative thereof is carried out using a catalyst. According to one embodiment, the catalyst is present on or with a support material. Suitable support materials include, without limitation, carbon (e.g., graphite, activate carbon, carbon black, carbon nanotube, graphene, and any of their functionalized derivatives), silicon dioxide, titanium oxide, zirconium oxide, cerium oxide, zinc oxide, zeolite, or mixtures thereof. By being "present on or with a support material" the catalyst may be contained in a reaction solution on the support material, attached or in contact with a surface of the support material, or part of the surface chemistry of the support material. Alternatively, converting levulinic acid or a derivative thereof is carried out using a catalyst that is added to a reactor containing the source of levulinic acid or a derivative thereof. For example, catalyst may be added drop-wise into the reactor, or may be mixed with the starting material before or during the conversion reaction in the reactor.

Converting levulinic acid or a derivative thereof according to this and other aspects of the present invention may be carried out in the presence of water. A suitable amount of water includes, without limitation, an equal amount of water to the amount of levulinic acid. Other amounts of water may be used, including water in a ratio of water to levulinic acid or a derivative thereof of about 1:1, 0.9:1, 0.8:1, 0.7:1, 0.6:1, 0.5:1, 0.4:1, 0.3:1, 0.2:1, 0.1:1, 0:1, 1:0.9, 1:0.8, 1:0.7, 1:0.6, 1:0.5, 1:0.4, 1:0.3, 1:0.2, or 1:0.1.

In another embodiment of this and other methods of the present invention, converting is carried out in the presence of formic acid. When carried out in the presence of formic acid, the formic acid may be present in the reactor in an amount of formic acid to levulinic acid or derivative thereof of about 0:1 (i.e., no formic acid), 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, or 2.0:1.

In carrying out this and other methods of the present invention, in addition to hydrocarbons, hydrogen is produced as a product. In yet another embodiment, carbon dioxide is also produced as a product.

Converting levulinic acid or a derivative thereof to hydrocarbons and hydrogen according to this and other methods of the present invention is carried out at temperature of about 200° C.-400° C., about 250° C.-350° C., or about 280° C.-320° C. While reaction temperatures may vary, as described herein, so too may the reaction times. For example, in carrying out this and other methods of the present invention, converting is carried out for a period of about 1 to about 24 hours, about 2 to about 23 hours, about 3 to about 22 hours, about 4 to about 21 hours, about 5 to about 20 hours, about 6 to about 19 hours, about 6 to about 12 hours, about 7 to about 11 hours, about 8 to about 10 hours, or about 9 hours.

In carrying out this and other methods of the present invention, converting is carried out in the reactor at a pressure of about 500 to about 5,000 psi, about 750 to about 4,500 psi, about 1,000 to about 4,000 psi, about 1,500 to about 3,500 psi, or about 2,000 to about 3,000 psi.

In the method of this and other aspects of the present invention, converting is carried out under an inert atmosphere. Alternatively, converting may be carried out in the presence of nitrogen gas, helium, argon, or carbon dioxide. In another embodiment, converting is carried out in the presence of a reducing agent selected from hydrogen, carbon monoxide, or a mixture thereof. In yet another embodiment, converting is carried out in the presence of hydrocarbons (e.g., n-hexadecane).

In carrying out this and other methods of the present invention, converting levulinic acid or a derivative thereof to hydrocarbons and hydrogen yields less than about 10% oxygenates, less than about 9% oxygenates, less than about 8% oxygenates, less than about 7% oxygenates, less than about 6% oxygenates, less than about 5% oxygenates, less than about 4% oxygenates, less than about 3% oxygenates, less than about 2% oxygenates, or less than about 1% oxygenates. The term "oxygenates" refers to chemical compounds that contain oxygen as a part of their chemical structure, except for carbon monoxide, carbon dioxide, and water.

In carrying out the method of this and other aspects of the present invention, converting levulinic acid or a derivative thereof to hydrocarbons and hydrogen results in an overall yield of at least about 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% hydrocarbons. Alternatively, converting levulinic acid or a derivative thereof to hydrocarbons results in an overall yield of about 60%-99% hydrocarbons or 70%-90% hydrocarbons.

In carrying out the method of this and other aspects of the present invention, when hydrogen is produced as a product, converting levulinic acid or a derivative thereof to hydrocarbons and hydrogen results in a hydrogen to hydrocarbon ratio of at least about 0.01, 0.05, 0.1, 0.15, 0.2, 0.25, 0.3, 0.35, 0.4, 0.45, or 0.5:1. The hydrogen to hydrocarbon ratio refers to the molar ratio of dihydrogen gas to carbon atoms of hydrocarbons.

As used herein, "hydrocarbons" includes aromatics, olefins (e.g., linear chain olefins), cycloalkenes, and saturated hydrocarbons (e.g., alkanes). For example, and without limitation, hydrocarbons produced according to this and the other methods of the present invention include olefins, aromatics, and alkanes comprising one or more of the following:

, and

Another aspect of the present invention relates to a method of producing hydrocarbons and hydrogen. This method involves providing a reactor that includes levulinic acid or a derivative thereof, water, and formic acid. The reactor or contents therein are heated under conditions effective to convert the levulinic acid or derivative thereof to hydrocarbons and hydrogen.

In carrying out this aspect of the present invention, in one embodiment, the reactor further comprises a metal or metal oxide catalyst as described supra.

Moreover, any and all descriptions related to the aspect of the invention described supra, are also applicable to the method of this aspect of the present invention.

Another aspect of the present invention relates to a method of producing hydrogen. This method involves providing a reactor that includes levulinic acid or a derivative thereof, water, and formic acid. The reactor or contents therein are heated under conditions effective to convert the levulinic acid or a derivative thereof, water, and formic acid to hydrogen.

Yet another aspect of the present invention relates to a method for producing hydrocarbons and hydrogen from biomass. This method involves providing lignocellulosic biomass; reacting the biomass with reagents under conditions effective to produce levulinic acid or a derivative thereof and converting the levulinic acid or derivative thereof to hydrocarbons and hydrogen, where the converting is carried out in a single reactor.

In carrying out this aspect of the present invention, reacting biomass with reagents under conditions effective to produce levulinic acid or a derivative thereof are well known in the art. See, e.g., Rackemann & Doherty, "The Conversion of Lignocellulosics to Levulinic Acid," *Biofuels, Bio-products, and Biorefining* 5(2):198-214 (2011), which is hereby incorporated by reference in its entirety.

Further, any and all descriptions related to the aspects of the invention described supra, e.g., with respect to converting levulinic acid or a derivative thereof to hydrocarbons and hydrogen, are also applicable to the method of this aspect of the present invention.

A further aspect of the present invention relates to a method for producing hydrocarbons and hydrogen from biomass. This method involves providing lignocellulosic biomass and reacting the biomass with reagents under conditions effective to produce levulinic acid or a derivative thereof. A reactor is provided that includes the levulinic acid or a derivative thereof, water, and formic acid. The reactor or contents therein is heated under conditions effective to convert the levulinic acid or derivative thereof to hydrocarbons and hydrogen.

Any and all descriptions related to the aspects of the invention described supra, are also applicable to the method of this aspect of the present invention.

EXAMPLES

Example 1—The Conversion of Levulinic Acid to Hydrocarbons and Hydrogen I

Experimental Conditions

The conversion of levulinic acid to hydrocarbons and hydrogen was carried out in a 100 mL Parr 4590 high-pressure/high-temperature micro stirred reactor equipped with mechanical stirring. In a typical experiment, 0.5-2 g of catalyst, 15.0 g of levulinic acid (>97%, Sigma Aldrich), and 15.0 g deionized water were added into a glass liner, which was placed in the vessel. Formic acid (5.9 g; formic acid/levulinic acid=1 molar ratio) was added. The reactor was purged with $N_2$ (99.997%) three times, and finally sealed at a $N_2$ pressure of 10 bar. After maintaining the reaction at the target temperature for a certain amount of time, the reaction was terminated by ceasing mechanical stirring and removing the furnace.

After cooling down to room temperature, the gaseous product was collected in a gas sample bag, and analyzed using gas chromatography ("GC") and gas chromatography mass spectrography ("GC-MS"). The amounts of carbon dioxide and other hydrocarbons in the gaseous sample were determined using nitrogen as the internal standard on the same GC system equipped with a packed column (HAYESEP D, 15 FT×⅛", 100/120 mesh), a 10-way sampling valve, and a thermal conductivity detector. The amount of hydrogen was determined using an external standard on the same GC system. The amounts of hydrocarbons in the gaseous sample were also analyzed on a HP 5890 GC system equipped with a capillary column (HP-PLOT Q, 30 m×0.32 mm×20.0 µm), a 10-way sampling valve and a flame ionization detector. 1-Butene, trans-2-butene, and cis-2-butene were identified using an on-line mass spectrometer (Agilent 5973N) connected to the outlet of the thermal conductivity detector of a GC system.

The liquid phase, also containing solids, was collected in centrifuge tubes. After centrifugation at 8,000 rpm for 10 minutes, the oily layer, the aqueous layer, and solid precipitate were separated. The solid precipitate was extracted with 10 mL acetone 3 times. The extracted solution was combined and then analyzed using GC and GC-MS. The solid precipitate was dried in an oven at 110° C. overnight and then weighed. The yield of humin was calculated using the change in the mass of solids before and after reaction.

Liquid phase products, including oily layer, aqueous layer, and extracted acetone solution, were analyzed using GC and GC-MS. Around 100 μL of 3-methyl-2-butanone (Aldrich, 99%) and 100 μL of 1,4-dioxane (Fisher Scientific) were added into the oily layer, aqueous layer, or extracted acetone solution as internal standards.

The components in liquid phase were identified on a GC-MS system (Agilent 6890N GC/5975N MSD) equipped with a capillary column (HP-5 ms, 30 m×0.32 mm×0.25 μm). For quantitative analysis, a calibration standard solution containing 2-butanone, gamma-valerolactone ("GVL"), levulinic acid, 3-methyl-2-butanone, 1,4-dioxane, cyclohexene (Alfa Aesar), m-xylene (99+%, Acros Organics), and hexadecane (Sigma-Aldrich) was prepared to determine the response factor of the products.

The amounts of levulinic acid and GVL were measured on a HP 5890 GC system equipped with a capillary column (DB-WAXetr, 30 m×0.25 mm×0.25 μm), which can provide better resolution for levulinic acid detection.

The yield of humin was calculated using the change in the mass of solids before and after reaction.

The aqueous phase products were separated and subjected to vacuum distillation to remove water. The remaining residue was dark brown liquid or tar. These byproducts could come from side reactions of levulinic acid conversion and was therefore considered in a carbon balance calculation (assume it has the same elemental composition as levulinic acid). Carbon balance was calculated using the total amount of carbon detected from GC analysis of the products after reaction, including $CO_2$, C1-C4 gaseous products, C4+ hydrocarbons in liquid phase, divided by the total amount of carbon from levulinic acid and formic acid. The CHN elemental analysis was carried out on a Perkin Elmer 2100 Series II CHN/S Analyzer. $^1H$ and $^{13}C$ NMR analysis of oily products was carried out using a Varian MR-400 NMR instrument.

Results

Figure 1:
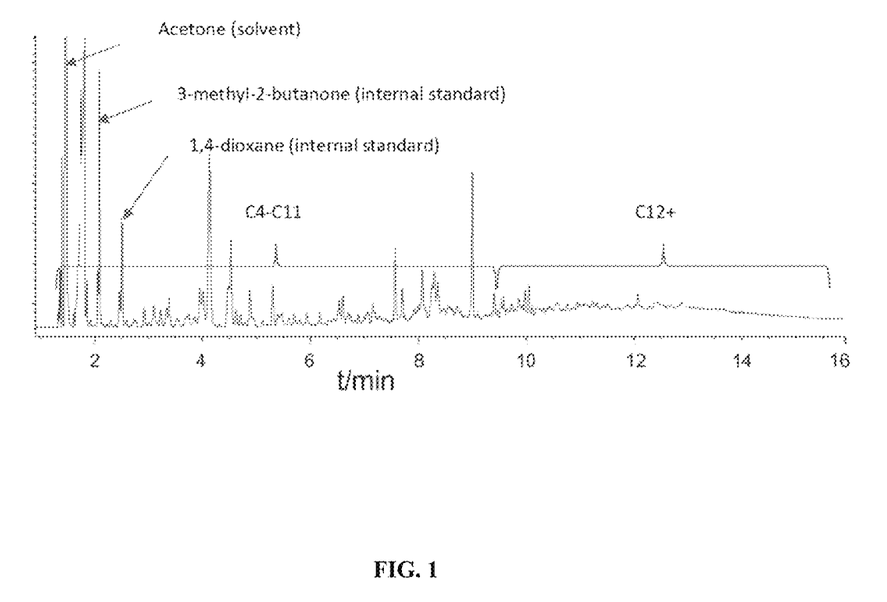
FIG. 1 shows GC spectrum of oil layer products. The samples were diluted with acetone. 100 µL of 3-methyl-2-butanone and 100 µL of 1,4-dioxane were used as internal standards. The typical components were identified by GC-MS, such as 2-butanone, 3,5-dimethylcyclopentene, 1,3-dimethylcyclohexene, 3,5-dimethylcyclohexene, 1,4-dimethylcyclohexene, 3-methylcyclopentanone, xylenes, GVL, 2,3-dimethylcyclopentanone, tetrahydrodimethylnaphthalene, etc. (listed by retention time).

The results indicated that in all cases levulinic acid could be converted to olefins, aromatics (shown in FIGS. 1 and 2), hydrogen, and carbon dioxide in one pot (Scheme 1), on the basis of GC and GC-MS analysis.

Scheme 1. Conversion of cellulosic biomass to unsaturated hydrocarbons (olefins and aromatics), hydrogen and carbon dioxide in two steps. Hydrocarbon products can be used as "drop-in" transportation fuels.

Example 2—The Conversion of Levulinic Acid to Hydrocarbons and Hydrogen II

Figure 2:
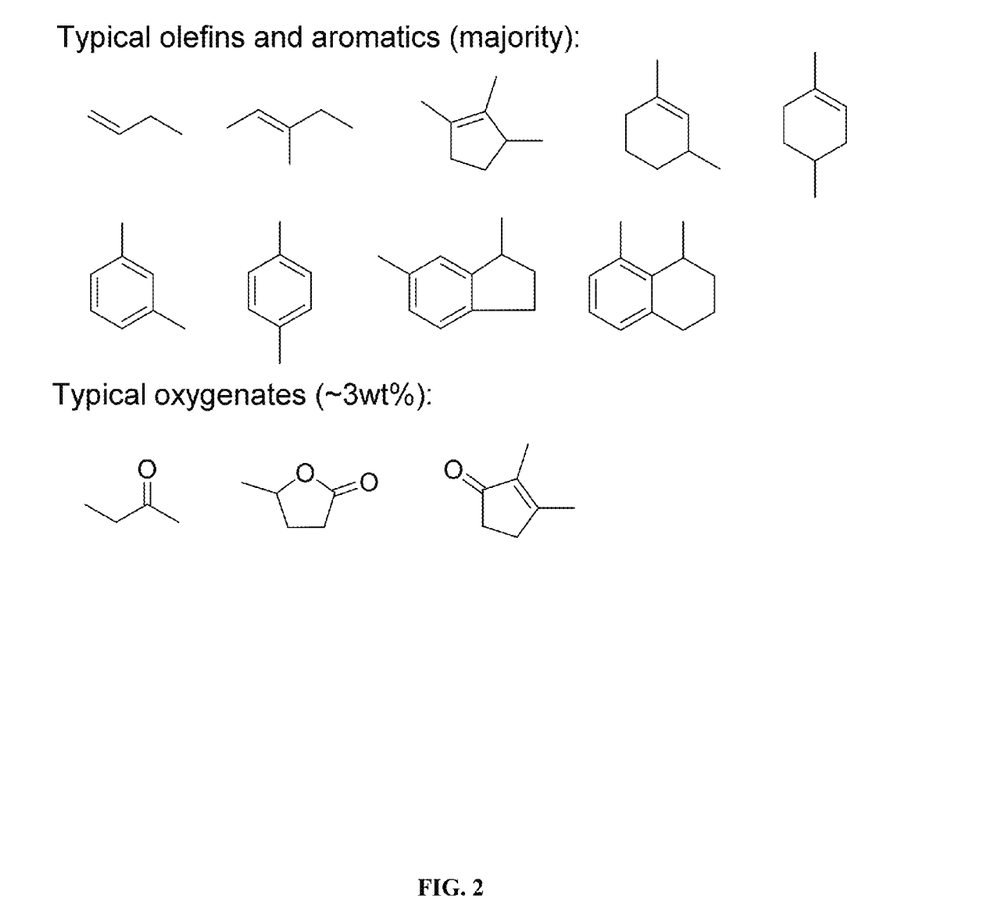
FIG. 2 shows the chemical structures of representative C4+ products obtained from the conversion of levulinic acid in the presence of NiSn/SiO$_2$ catalyst. The structures were determined by gas chromatography mass spectrography ("GC-MS") analysis.
Figure 4:
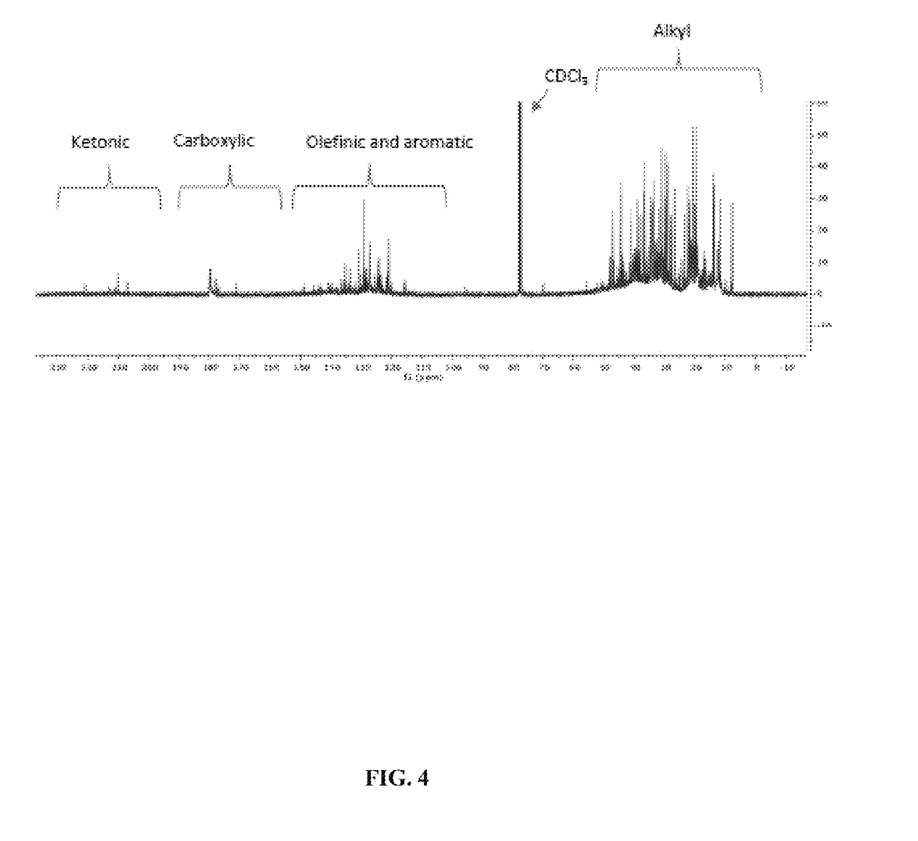
FIG. 4 shows $^{13}$C NMR of oily product. CDCl$_3$ was used as the solvent. The major component (>97%) of carbon is olefinic, aromatic, and alkyl carbon. The amount of ketonic and carboxylic carbon is less than 3%.
Figure 5:
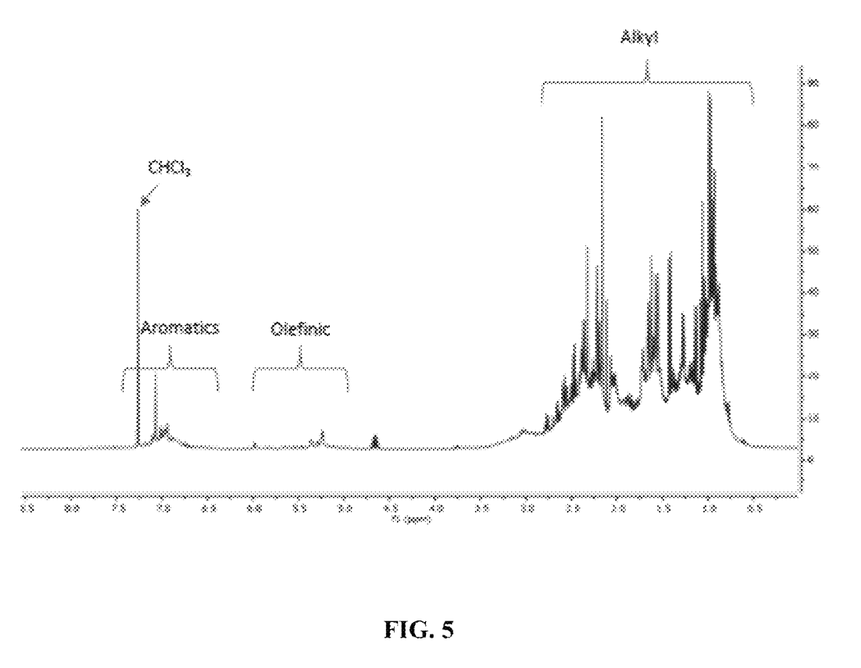
FIG. 5 shows $^1$H NMR of oily products. CDCl$_3$ was used as the solvent. The major component of hydrogen is also olefinic, aromatic, and alkyl hydrogen, which agrees with the $^{13}$C NMR of the oily product.

In another experiment, levulinic acid (15 g; 0.13 mol), formic acid (6.9 g; 0.13 mole), water (15 g), and 10 wt % $NiSn/SiO_2$ catalyst (1.0 g) were mixed and heated to 300° C. in a high pressure vessel. The reactants were kept at this temperature for 12 hours. After reaction, a phase separation in the product solution which included a hydrocarbon phase at the upper layer (~5 g) and an aqueous phase at the bottom layer (~18 g) (FIG. 3) was observed. The products from oily layer, aqueous phase, and gas phase were analyzed with GC and GC-MS. The yield of C4+ hydrocarbons was calculated. It was found that the overall yield of C4+ hydrocarbon products can reach 60-90% of the theoretical value during several parallel runs. Based on GC-MS analysis, it was found that the oily products mainly included olefins and monocyclic aromatics (~97 wt %), such as 3,5-dimethylcyclopentene, 1,3-dimethylcyclohexene, 3,5-dimethylcyclohexene, 1,4-dimethylcyclohexene, xylene, and tetrahydrodimethylnaphthalene (FIG. 2). Only small amounts of oxygenates (~3 wt %), such as butanone, gamma-valerolactone, and 2,3-dimethylcyclopentanone, were detected. $^{13}C$ and $^1H$ NMR spectroscopy (FIGS. 4 and 5) revealed that major component of carbon (>97%) is olefinic, aromatic, and alkyl carbon. The amount of ketonic and carboxylic carbon is less than 3%.

Higher heating value of crude hydrocarbon products was measured to be 39.7 MJ/kg, which is close to those of benzene (41.9 MJ/kg) and biodiesel (40.2 MJ/kg), suggesting that the products are suited for use as transportation fuels.

Figure 3:
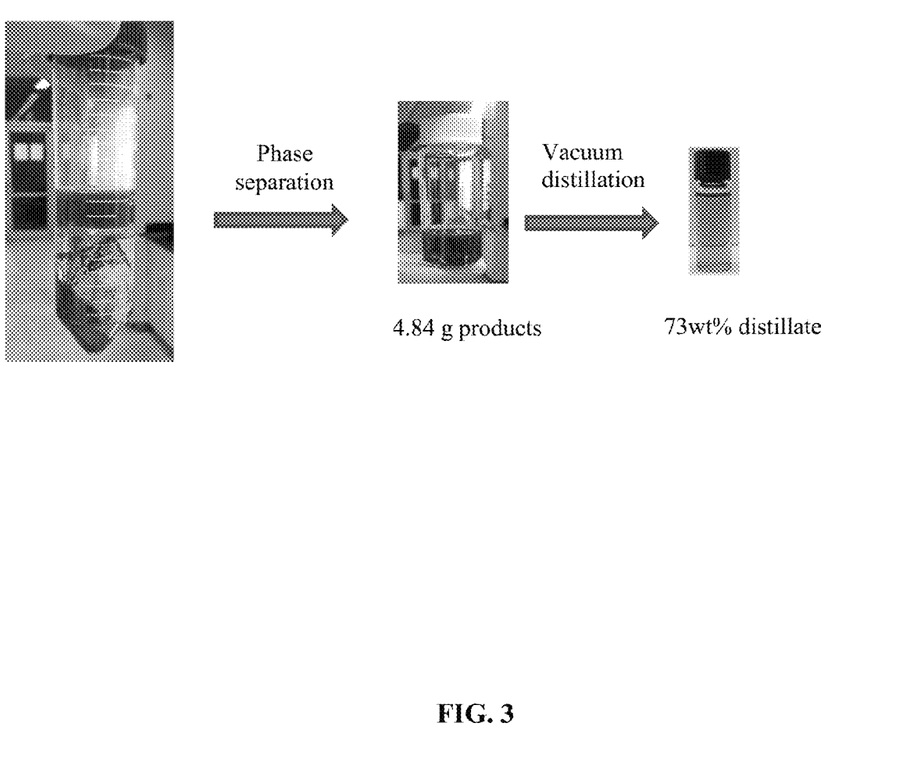
FIG. 3 shows images of products obtained after reaction. Reaction conditions: 1 g catalyst, 15 g levulinic acid, 15 g water, 5.9 g formic acid, 300° C., 12 hours. The left image shows the products after centrifugation. 4.84 g of oil products was obtained from the top layer. 73 wt % liquid was recovered from the oil products with distillation under reduced pressure (the remaining was wax residue).

Olefins and monocyclic aromatics are common components in conventional petroleum based gasoline, diesel, and jet fuels. Hence, in principle, the products obtained from the proposed process could be used as "drop in" gasoline, diesel, and jet fuels after distillation (Scheme 1). Vacuum distillation for the products was performed, and it was found that at least 73 wt % of the products can be separated with distillation (FIG. 3). These lower boiling point products can be directly used as "drop in" gasoline, diesel, and jet fuels when separated with appropriate boiling point range. The remaining residue (~27 wt %) is mainly wax product, which could be used as lubricants, coatings, etc.

Furthermore, it was found that butenes, hydrogen, and carbon dioxide are the major products in gas phase, based on GC analysis. It was determined that the amount of hydrogen is 0.11 mole, which is very close to the amount of levulinic acid reactant (0.13 mole). Hydrogen produced from this process is significant because hydrogen is required in many biomass conversion processes in order to remove excessive oxygen from cellulosic biomass. In the process described here, the production of hydrogen is mainly due to the formation of cycloalkenes and aromatics. The H/C ratio of oily products is 1.55, which was determined by CHNS elemental analysis.

Example 3—Influence of Water in the Conversion of Levulinic Acid to Hydrocarbons and Hydrogen It was found that water is necessary for the reaction set forth in Examples 1 and 2 above in order to obtain high yields, lighter color, and less viscosity for liquid products. When ethanol was used instead of water as the solvent and other reaction parameters are the same as those in Example 2, the product distribution was changed, where gamma-valerolactone and ethyl levulinate became the major products.

Example 4—Influence of Catalysts in the Conversion of Levulinic Acid to Hydrocarbons and Hydrogen A variety of catalysts, including 10% Mo/graphene, 10% Fe/graphene, 10% Co/graphene, 10% Ni/graphene, 10%

NiSn/SiO$_2$, 1% Ru-10% Ni/SiO$_2$, 1% Ru-10% NiSn/SiO$_2$, 10% NiSn/carbon black (Vulcan XC72), 10% NiSn/TiO$_2$, 5% Pt/CeO$_2$, 5% Pt/Ce$_{0.27}$Zr$_{0.73}$O$_2$ were tested using the same reaction condition as Example 2 (catalyst amount may vary). Those catalysts were prepared with wetness impregnating the corresponding metal salt precursors with appropriate support materials, followed by reduction at elevated temperatures (400-900° C.) under 10% hydrogen/helium flow. The results of levulinic acid conversion were shown in Table 1.

It was found that hydrocarbons and hydrogen could be obtained in all cases. In the absence of any catalysts though, the yield of C4+ hydrocarbon products is relatively low (56.2%) and the liquid products are more viscous (estimated with eye).

When suitable catalysts such as 10% NiSn/SiO$_2$, 1% Ru-10% Ni/SiO$_2$, 1% Ru-10% NiSn/SiO$_2$, 10% NiSn/TiO$_2$, 5% Pt/CeO$_2$, 5% Pt/Ce$_{0.27}$Zr$_{0.73}$O$_2$, 10% Ni/graphene, 10% Mo/graphene, MgO—SiO$_2$ (2:1 in molar ratio) and HZSM-5 zeolite were used, higher yields of hydrocarbon products could be obtained (>60%). The yield of hydrogen is typically in the range of 0.075-0.18 mole under current reaction conditions.

When 10% NiSn/carbon black (Vulcan XC72), 10% Fe/graphene, 10% Co/graphene was used as the catalyst, lower hydrocarbons yields were obtained. Moreover, high humin yields were found when 10% NiSn/carbon black (Vulcan XC72), 10% Mo/graphene, and MgO—SiO$_2$ (2:1 in molar ratio) were used as the catalyst. Therefore, selected catalysts may be better suited for use in this reaction.

TABLE 1

Summary of the Conversion of LA to Hydrocarbons and Hydrogen Over Various Catalysts

| Entry | Catalyst | Mass of catalyst (g) | Conversion (%) | H$_2$ (mol) | Yield of C4+ hydrocarbons (%) | Yield of Humin (%) |
|---|---|---|---|---|---|---|
| 1 | Blank | 0 | 96.8 | 0.17 | 56.2 | 0.9 |
| 2 | 10% NiSn/SiO$_2$ | 0.05 | 97.4 | 0.11 | 75.3 | 2.2 |
| 3 | 1% Ru—10% NiSn/SiO$_2$ | 1.0 | 97.3 | 0.078 | 85.6 | ND |
| 4 | 1% Ru—10% Ni/SiO$_2$ | 1.0 | 98.9 | 0.091 | 92.8 | 1.1 |
| 5 | 10% NiSn/carbon black (Vulcan XC72) | 0.2 | 97.7 | 0.10 | 15.7 | 13.1 |
| 6 | 10% NiSn/TiO$_2$ | 0.2 | 97.4 | 0.14 | 67.6 | 0.2 |
| 7 | 5% Pt/Ce$_{0.27}$Zr$_{0.73}$O$_2$ | 0.2 | 96.2 | 0.18 | 76.7 | 0.7302 |
| 8 | 5% Pt/CeO$_2$ | 0.2 | 97.2 | 0.16 | 73.6 | 0 |
| 9 | 10% Fe/graphene | 0.05 | 98.3 | 0.17 | 43.9 | 1.9 |
| 10 | 10% Co/graphene | 0.05 | 99.2 | ND | 38.7 | 1.5 |
| 11 | 10% Ni/graphene | 0.05 | 96.9 | ND | 61.4 | 1.0 |
| 12 | 10% Mo/graphene | 0.2 | 98.4 | 0.075 | 70.3 | 11.1 |
| 13 | MgO—SiO$_2$ | 0.2 | 99.9 | 0.12 | 74.3 | 28.7 |
| 14 | HZSM-5 | 0.2 | 96.7 | 0.057 | 98.0 | 0.5 |

ND: not determined.

Example 5—Influence of Formic Acid in the Conversion of Levulinic Acid to Hydrocarbons and Hydrogen The influence of formic acid was studied in the absence of catalyst. In the experiment, 15 g of levulinic acid, 0 g or 5.9 g of formic acid, and 15.0 g water were added together. The mixture was heated to 300° C. under 10 bar N$_2$, and kept at this temperature for 24 hours. After reaction, the similar yields of C4+ hydrocarbons (54.5 and 61.7%) and humin (4.1 and 5.2%) were obtained. The major difference is the amount of generated hydrogen. Significantly more hydrogen (0.096 mole vs 0.024 mole) could be obtained after adding formic acid.

TABLE 2

Influence of Formic Acid

| Entry | Catalyst | Formic acid (g) | Conversion (%) | H$_2$ (mol) | Yield of C4+ hydrocarbons (%) | Yield of Humin (%) |
|---|---|---|---|---|---|---|
| 1 | No catalyst | 0 | 97.1 | 0.024 | 54.5 | 4.1 |
| 2 | No catalyst | 5.9 | 99.6 | 0.096 | 61.7 | 5.2 |

Example 6—Influence of Reaction Temperature in the Conversion of Levulinic Acid to Hydrocarbons and Hydrogen The influence of reaction temperature was studied in the absence of catalyst. In the experiment, 15 g of levulinic acid, 5.9 g of formic acid, and 15.0 g water were added together. The mixture was heated to target temperature (240, 270, or 300° C.) under 10 bar N$_2$, and kept at this temperature for 12 hours. It was found that the conversion of levulinic acid, the amount of generated hydrogen, the yield of C4+ hydrocarbons, and the yield of humin increased with rising reaction temperatures. The conversion of levulinic acid is almost complete at 300° C. even in the absence of catalyst.

TABLE 3

Influence of Reaction Temperature

| Entry | Catalyst | Temperature (° C.) | Conversion (%) | H$_2$ (mol) | Yield of C4+ hydrocarbons (%) | Yield of Humin (%) |
|---|---|---|---|---|---|---|
| 1 | No catalyst | 240 | 92.1 | 0.033 | 27.8 | 0 |
| 2 | No catalyst | 270 | 93.6 | 0.10 | 48.0 | 0.5 |
| 3 | No catalyst | 300 | 96.8 | 0.17 | 56.2 | 0.9 |

Figure 6:
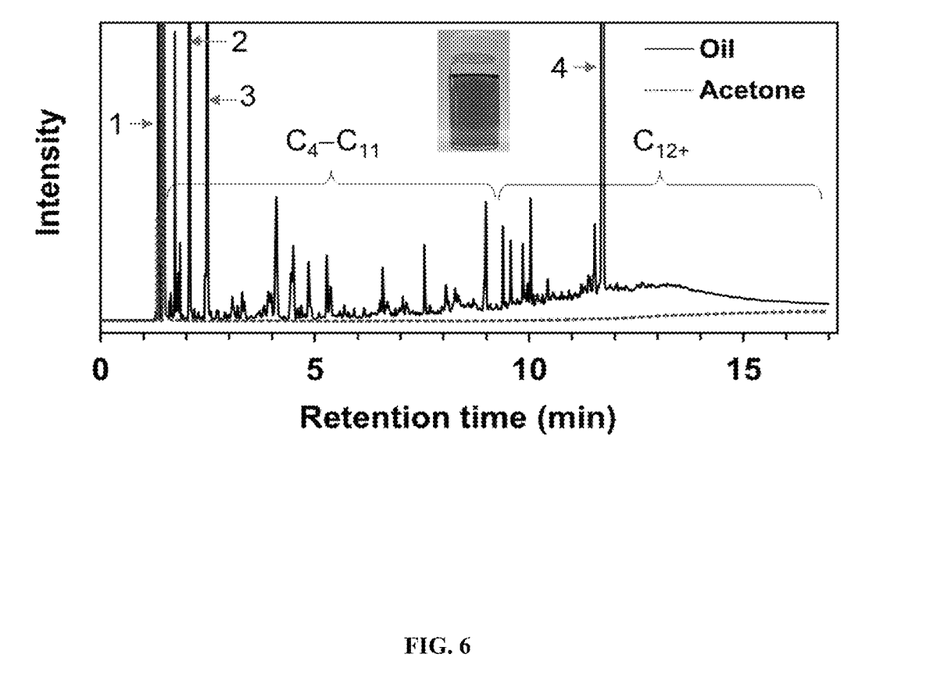
FIG. 6 shows gas chromatography ("GC") spectra of the oil sample (solid line) and acetone (blank sample; dashed line) obtained on nonpolar HP-5 capillary column. The oil sample was diluted with acetone before GC analysis. N-hexadecane was added before the reaction as the solvent. 1: acetone; 2: 3-methyl-2-butanone (internal standard); 3: 1,4-dioxane (internal standard); 4: n-hexadecane. Inset picture: Oil layer sample obtained after reaction (14.7 g in total; containing approximately 4.7 g oil products and 10 g n-hexadecane). The picture was not subjected to any artificial adjustment to retain its natural appearance.

Example 7—Influence of Hydrophobic Solvent in the Conversion of Levulinic Acid to Hydrocarbons and Hydrogen The influence of hydrophobic solvent was studied by adding 10 g n-hexadecane to the mixture containing 15 g of levulinic acid, 5.9 g of formic acid, 15.0 g water, and 1.0 g 10% NiSn/SiO$_2$ catalyst. A bi-phase system was formed which contains n-hexadecane as the top layer and aqueous solution as the bottom layer (Table 4, entries 6-9). It was found that the top layer gained weight (~15 g) after the reaction at 320° C. for 12 hours, indicating that oily products formed. The top layer products showed light brownish color, suggesting that less heavy products formed (inset picture in FIG. 6). GC and GC-MS analysis showed that the similar products were obtained after the addition of n-hexadecane (FIG. 6). 68.3% of theoretical yield for C4+ products was obtained at the first run. This 10% NiSn/SiO$_2$ catalyst was reused for at least 4 runs, without any loss in conversion or oil yield. Moreover, produced hydrogen was in the range of 0.084-0.14 mole.

TABLE 4

Influence of Hydrophobic Solvent

| Entry | Catalyst | Mass of catalyst (g) | Conversion (%) | H$_2$ (mol) | Yield of C4+ hydrocarbons (%) | Yield of Humin$^a$ (%) |
|---|---|---|---|---|---|---|
| 1 | 10%NiSn/SiO$_2$, 1$^{st}$ run | 1.0 | 100.0 | 0.084 | 68.3 | ND |
| 2 | 10%NiSn/SiO$_2$, 2$^{nd}$ run | 1.0 | 95.3 | 0.14 | 69.9 | ND |
| 3 | 10%NiSn/SiO$_2$, 3$^{rd}$ run | 1.0 | 100.0 | 0.12 | 66.0 | ND |
| 4 | 10%NiSn/SiO$_2$, 4$^{th}$ run | 1.0 | 94.9 | 0.14 | 77.5 | 7.6 |

ND: not determined.
$^a$The 7.6% of humin is the total amount generated during 4 recycle runs. The catalysts after the 1$^{st}$, 2$^{nd}$, and 3$^{rd}$ recycle runs were not dried. Therefore the yields of humin in the 1$^{st}$, 2$^{nd}$, and 3$^{rd}$ recycle runs were not calculated.

What is claimed:

1. A method of converting levulinic acid or a derivative thereof to hydrocarbons and hydrogen, said method comprising:
   providing a source of levulinic acid or a derivative thereof and
   converting levulinic acid or a derivative thereof in the source to hydrocarbons and hydrogen, wherein said converting is carried out in a single reactor.

2. The method according to claim 1, wherein said converting is carried out in the presence of a catalyst.

3. The method according to claim 2, wherein the catalyst is selected from a metal, metal oxide, zeolite, or mixture thereof.

4. The method according to claim 3, wherein the catalyst is selected from Fe, Co, Ni, Ru, Sn, Mo, Pt, or a mixture thereof.

5. The method according to claim 2, wherein said catalyst is present on a support material.

6. The method according to claim 5, wherein the support material is selected from carbon, graphene, silicon dioxide, titanium oxide, zirconium oxide, cerium oxide, zeolite, or a mixture thereof.

7. The method according to claim 1, wherein said converting is carried out in the presence of water.

8. The method according to claim 1, wherein said converting is carried out in the presence of formic acid.

9. The method according to claim 1, wherein carbon dioxide is produced as a product.

10. The method according to claim 1, wherein said converting is carried out at temperature of about 200-400° C.

11. The method according to claim 1, wherein said reactor is a high pressure vessel.

12. The method according to claim 1, wherein said reactor is a flow reactor.

13. The method according to claim 1, wherein said converting is carried out at a pressure of about 500-5000 psi.

14. The method according to claim 1, wherein said converting is carried out under an inert atmosphere.

15. The method according to claim 14, wherein said converting is carried out in the presence of nitrogen gas, helium, argon, or carbon dioxide.

16. The method according to claim 1, wherein said converting is carried out in the presence of a reducing agent selected from hydrogen, carbon monoxide, or a mixture thereof.

17. The method according to claim 1, wherein said converting is carried out in the presence of hydrocarbons.

18. The method according to claim 1, wherein said converting is carried out for a period of about 1 to about 24 hours.

19. The method according to claim 1, wherein said converting yields less than about 10% oxygenates.

20. The method according to claim 1, wherein said converting results in an overall yield of 60-99% hydrocarbons.

21. The method according to claim 1, wherein said hydrocarbons comprise olefins, aromatics, and alkanes.

22. The method according to claim 21, wherein said olefins, aromatics, and alkanes comprise one or more of the following:

23. The method according to claim 1, wherein levulinic acid is converted to hydrocarbons.

24. The method according to claim 1, wherein levulinate ester is converted to hydrocarbons.

25. A method of producing hydrocarbons and hydrogen, said method comprising:
   providing a reactor comprising:
      levulinic acid or a derivative thereof;
      water; and
      formic acid and
   heating the reactor or contents therein under conditions effective to convert the levulinic acid or derivative thereof to hydrocarbons and hydrogen.

26. The method according to claim 25, wherein the reactor further comprises a metal or metal oxide catalyst.

27. The method according to claim 25, wherein said heating is carried out to a temperature of about 200-400° C.

28. The method according to claim 25, wherein said heating is carried out for about 1 to about 24 hours.

29. A method for producing hydrocarbons and hydrogen from biomass, said method comprising:
   providing lignocellulosic biomass;
   reacting the biomass with reagents under conditions effective to produce levulinic acid or a derivative thereof; and
   converting the levulinic acid or derivative thereof to hydrocarbons and hydrogen, wherein said converting is carried out in a single reactor.

* * * * *